(12) United States Patent
Neftel

(10) Patent No.: US 7,553,304 B2
(45) Date of Patent: Jun. 30, 2009

(54) MEDICAL DEVICE FOR INJECTING LIQUIDS

(75) Inventor: Frederic Neftel, Lausanne (CH)

(73) Assignee: SMC-Swiss Medical Care S.A., Lausanne (CH)

( * ) Notice: Subject to any disclaimer, the term of this patent is extended or adjusted under 35 U.S.C. 154(b) by 67 days.

(21) Appl. No.: 10/777,342

(22) Filed: Feb. 12, 2004

(65) Prior Publication Data

US 2004/0167495 A1  Aug. 26, 2004

Related U.S. Application Data

(62) Division of application No. 09/331,350, filed as application No. PCT/FR97/02341 on Dec. 18, 1997, now Pat. No. 6,716,193.

(30) Foreign Application Priority Data

Dec. 18, 1996 (FR) .................. 96 15551

(51) Int. Cl.
*A61M 31/00* (2006.01)
(52) U.S. Cl. ...................... 604/500; 604/535
(58) Field of Classification Search ............... 604/500, 604/540, 290, 892.1, 118, 247, 31, 67, 30, 604/183, 535, 151
See application file for complete search history.

(56) References Cited

U.S. PATENT DOCUMENTS

| 4,187,057 | A |   | 2/1980  | Xanthopoulos |
|-----------|---|---|---------|--------------|
| 4,464,172 | A | * | 8/1984  | Lichtenstein ................ 604/65 |
| 5,423,751 | A |   | 6/1995  | Harrison et al. |
| 5,533,978 | A | * | 7/1996  | Teirstein .................... 604/183 |
| 5,533,996 | A |   | 7/1996  | Murphey et al. |
| 5,549,566 | A |   | 8/1996  | Elias et al. |
| 5,569,181 | A | * | 10/1996 | Heilman et al. ............... 604/30 |
| 5,569,208 | A |   | 10/1996 | Woelpper et al. |
| 5,843,037 | A | * | 12/1998 | Uber, III ..................... 604/151 |

FOREIGN PATENT DOCUMENTS

| EP | 0 648 513 | 4/1995 |
|----|-----------|--------|
| EP | 0 650 739 | 5/1995 |

\* cited by examiner

*Primary Examiner*—Kevin C Sirmons
*Assistant Examiner*—Phillip Gray
(74) *Attorney, Agent, or Firm*—Wolf, Greenfield & Sacks, P.C.

(57) ABSTRACT

The invention relates to a device for injecting liquid, comprising a piece of tubing on which there is situated at least a first liquid occlusion system. According to the invention, a regulation system (4) is situated upstream from the first occlusion system, the two systems defining an intermediate segment in which the pressure, in the absence of injection, is greater than the pressure that exists downstream from the first occlusion system so as to direct any leak of liquid from the first occlusion system downstream. The invention is applicable to a pump used for injecting contrast liquid for medical imaging.

13 Claims, 5 Drawing Sheets

MEDICAL DEVICE FOR INJECTING LIQUIDS

RELATED APPLICATIONS

This application claims the benefit of and is a divisional of co-pending U.S. patent application Ser. No. 09/331,350, filed on Jun. 17, 1999, which is a national phase application of PCT/FR97/02341, filed Dec. 18, 1997, which claims priority from FR 96/15551, filed Dec. 18, 1996.

BACKGROUND OF INVENTION

1. Field of the Invention

The present invention relates to a medical device for injecting liquid.

An application for such a device can lie, for example, with a pump used for injecting contrast liquid for medical imaging.

2. Discussion of Related Art

A major problem that results from injecting liquid into patients lies in the risk of the injection device being contaminated by the patient. When a liquid is administered to a patient, there is a risk of the injected liquid flowing back after it has already come into contact with the patient. Also, in the absence of injection, there still exists a risk of contamination by contaminating agents, such as germs, migrating from the patient to the injection device. As a general rule, this situation makes it essential, when treating a new patient, to change all of the portions of the device that have already been used.

There exist several devices in the prior art for reducing the risk of such backflow: EP-A-64853 in the name of MEDEX S. A. describes an injection unit that includes a non-return valve, for example. EP-A-279028 in the names of KABI PHARMACIA GmbH and PFRIMMER-VIGGO GmbH claims a liquid injection device having a non-return valve characterized by the fact that the opening pressure can be set to either of two positions.

Although prior art devices do indeed reduce the risk of backflow, there still remains the risk of the non-return valve leaking. This risk is particularly high in the absence of injection.

SUMMARY OF INVENTION

The present invention thus seeks totally to eliminate any risk of backflow. In addition, the present invention also seeks to make it possible to detect any leak through the safety means that are installed to avoid such backflow, assuming such backflow might indeed take place.

To this end, use is made of a device for injecting liquid, the device comprising a piece of tubing on which there is situated at least a first liquid occlusion system such as a non-return valve. In addition, a regulation system is situated upstream from the first occlusion system, the two systems defining an intermediate segment in which the pressure, in the absence of injection, is greater than the pressure that exists downstream from the first occlusion system. In this way, any leak of liquid at the first occlusion system is directed downstream and any leak from the intermediate segment can be detected by measuring the associated pressure drop.

The terms "downstream" and "upstream" mean respectively towards the patient and in the opposite direction.

By way of example, the regulation system can be a second non-return valve or a system for flattening the tubing, such as the wheels of the peristaltic cassette corresponding to patent FR 89/03234 in the name of MALBEC S. A.

It should be observed that the regulation system cannot be considered merely as constituting a safety system in addition to and independent of the first occlusion system.

On the contrary, the two systems together constitute an interactive assembly since the presence of the regulation system makes it possible to set up, and optionally to maintain, a positive pressure difference between the two systems to prevent any leakage of liquid located downstream from the first occlusion system from flowing upstream towards the intermediate segment.

It should also be observed that the pressure difference between the two systems is constant in the absence of a leak since the space between the two systems is filled with liquid which, like any other liquid, is incompressible.

In order to increase the safety of the device, it is also desirable to have systems of different kinds. As a result, if one system should fail, the other can nevertheless continue to act, in a manner similar to that described in the prior art.

Furthermore, when using systems of different kinds, and more precisely systems characterized by the fact that each of them has a different opening pressure, it is possible to direct the flow direction of the liquid in the event of a leak or high pressure in the intermediate segment.

In particular, if the opening pressure of the first occlusion system is less than the opening pressure of the regulation system, any liquid movement during an interruption of injection will take place downstream, the regulation system closing before the first occlusion system, thereby avoiding any contamination of the portions of the device situated upstream from the first occlusion system.

Similarly, in the event of high pressure in the intermediate segment, the first occlusion system will be the first to open in the event of a leak, thereby causing the liquid to go downstream from the first occlusion system and thus preventing any backflow towards the intermediate segment.

It is also possible to envisage that the two opening pressures of the regulation systems are identical, however that can only be envisaged if the opening pressure is greater than the pressure that exists downstream from the first occlusion system when there is no injection.

In addition, it is desirable to have an opening pressure for the first occlusion system which is greater than the maximum pressure that can be set up downstream therefore because of the patient in the absence of injection. Also, in the absence of injection, it is necessary for the opening pressure of the first occlusion system to be greater than the pressure of the intermediate segment.

In most cases, in the absence of injection, the pressure that exists downstream from the first occlusion system corresponds to the venous pressure of the patient.

In another preferred embodiment, it is desirable to provide the tubing with a disconnection system situated between the two regulation systems. The disconnection system marks the boundary between a downstream tubing for single use only and an upstream tubing for multiple use.

Thus, when the tubing is contaminated only downstream from the disconnection system, it is possible to change only that portion of the device while reusing the remainder thereof (pumping system, peristaltic cassette, reservoir, etc.) with other patients.

The disconnection system is preferably situated as close as possible to the second regulation device or, which comes to the same thing, as far as possible from the non-return valve. Thus, in the highly improbable event of contamination propagating upstream, the risk of contaminating the zone situated upstream from the disconnection system is minimized since the path to be followed to reach the disconnection system is as long as possible.

In another preferred embodiment, the disconnection system is provided with occlusion means for the tubing which are activated prior to disconnection, thereby avoiding any risk of liquid being ejected from the tubing which is under pressure. Such an automatic closure system is described, for example, in U.S. patents U.S. Pat. Nos. 5,549,566 and 5,533,996 in the names of ABBOTT LAB and BAXTER INT. INC., respectively.

The above-mentioned occlusion means can also be designed so as to open during connection.

By way of example, such disconnection systems can be of the "luer-lock" type coupled to a rotary cock system on each of the two connected segments. In addition, the connection system between the two pieces can be of the key and lock type, thus allowing interconnection to take place only between two elements that are properly encoded relative to each other. Such a rotary system makes it possible to open and close the two cocks placed on either side of the connection when the key is turned in the lock, while preventing the two pieces from being disconnected when the key is engaged in the position corresponding to the open position of the occlusion systems.

The occlusion system situated in the downstream segment can also be a non-return valve, and the system in the upstream segment can be a check valve that is open when the two pieces are engaged or, alternatively, the two occlusion systems can be check valves that are open only when the two pieces are engaged.

In another preferred embodiment, a pressure sensor is situated on the intermediate segment. As a result, it is possible to detect any pressure variation in this zone.

When the pressure sensor comes back into contact with the tubing, it is advantageous to place it between the disconnection system and the regulation system; this configuration has the merit of making it possible to reuse the same pressure sensor configuration for a plurality of patients.

In the absence of injection, any pressure drop between the two systems implies that a leak is present which, very likely, might have taken place in the first occlusion system or in the regulation system.

If the leak has taken place in the first occlusion system, then contamination can propagate into the tubing for multiple use.

If the leak has taken place in the regulation system, then contamination has not necessarily propagated into the tubing for multiple use, but the risk of that happening has nevertheless been increased since any leak at the first occlusion system gives rise to a drop in pressure in the intermediate segment, thus eliminating the effect of the means installed in the context of the present invention.

In order to mitigate the two above-described situations, it is advantageous to associate an alarm 102 with the pressure sensor placed on the intermediate segment. Furthermore, in even more advantageous manner, liquid injection can be triggered as to reestablish the initial pressure when the alarm is activated.

It should also be observed that maintaining a high pressure in the intermediate segment, close to the pressure for opening the first occlusion system, can serve to favor leakage at said first occlusion system.

To this end, means are provided to reduce the pressure in the intermediate segment. These means can be constituted by an intermediate chamber of adjustable volume. By way of example, the volume of the intermediate chamber can be adjusted by a piston. Thus, the pressure which exists in the intermediate segment can be selected so as to be greater than the pressure downstream from the first occlusion system and far enough away from the opening pressure of said first occlusion system to make full use of the sealing characteristics of said first occlusion system. Another means enabling said pressure to be lowered below the opening threshold of the first occlusion system consists in selecting a regulation system whose opening can be adjusted in such a manner as to lower the pressure of the intermediate segment to a predetermined value.

Although adjusting the pressure in the intermediate segment considerably reduces any risk of contamination, it is still possible after an alarm is triggered to change the portions that might have been contaminated, for example portions such as the peristaltic cassette. Under such circumstances, it is advantageous for this purpose to provide a second disconnection system upstream from the regulation system.

Optionally, a second pressure sensor can be placed on the segment of tubing which is to be found downstream from the first occlusion system, thus making it possible, for example, to detect any excess pressure compared with the pressure in the intermediate segment.

It is also possible to provide the device with a system for measuring the pressure difference as measured by the two sensors, thus having the advantage of determining the risk of backflow more directly. An alarm can be triggered when the pressures situated upstream and downstream of the non-return valve are tending to become equal.

The medical device of the invention can also be designed in such a manner as to deactivate the alarm when the single-use tubing is disconnected.

The medical device of the invention may advantageously include a syringe driver 100. A pressure sensor 108 can be placed on the distal end of the piston 106 of the syringe driver.

Assuming that a syringe driver 100 is used, it is possible to consider the syringe 104 itself as being an integral portion of the intermediate segment, and the syringe itself can form the regulation system. In addition, under these circumstances, the syringe 104 can also act as a system for regulating the intermediate chamber so as to enable the pressure in the intermediate chamber to be adjusted.

The medical device of the invention can be used with any type of liquid, and in particular it can be used for injecting contrast liquids.

BRIEF DESCRIPTION OF DRAWINGS

The invention is described below by way of an example and with reference to the accompanying drawings, in which:

FIGS. 2'A and 2'B correspond to the steps of FIGS. 2A and 2B when the disconnection system is used on subsequent occasions;

DETAILED DESCRIPTION

Figure 1A:
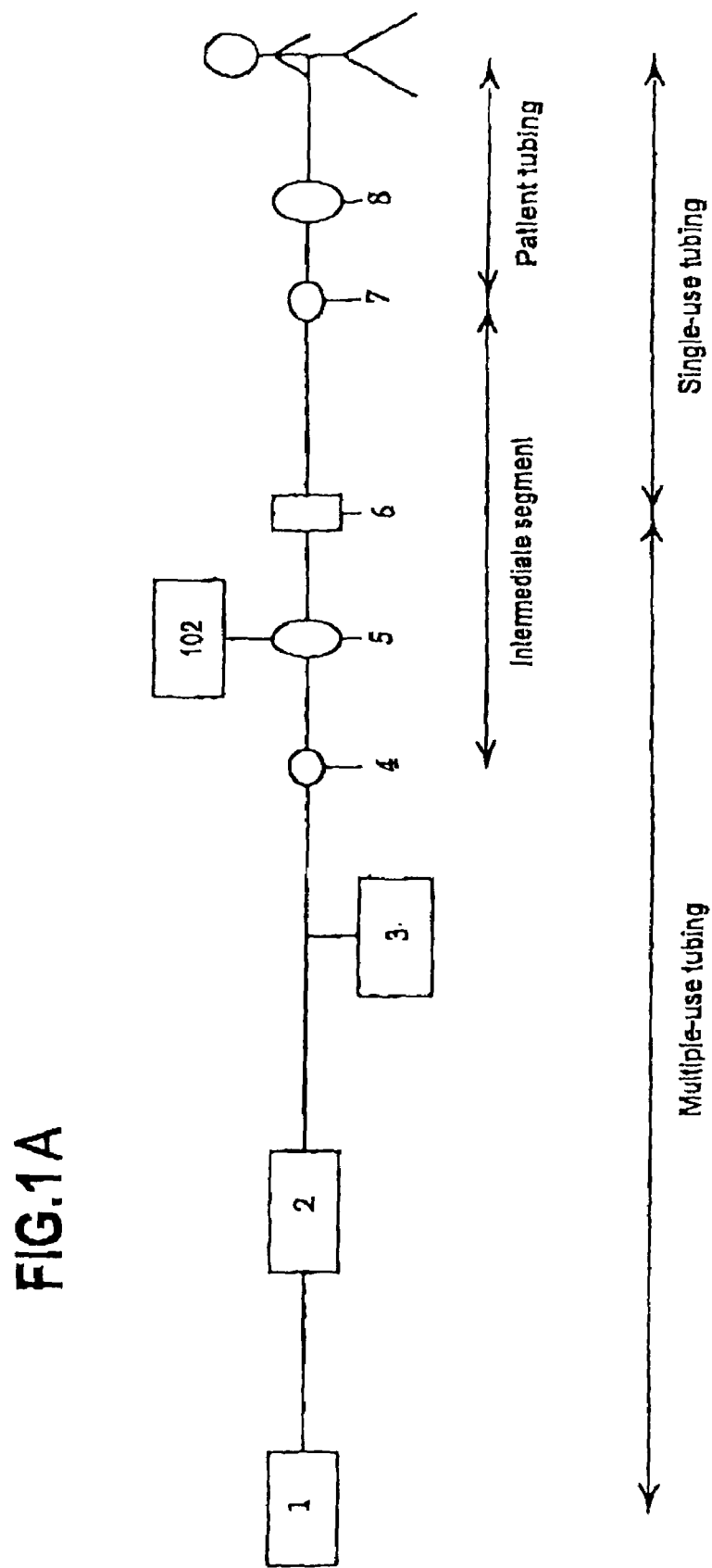
FIG. 1A is a diagram showing a preferred embodiment of the invention.
Figure 1B:
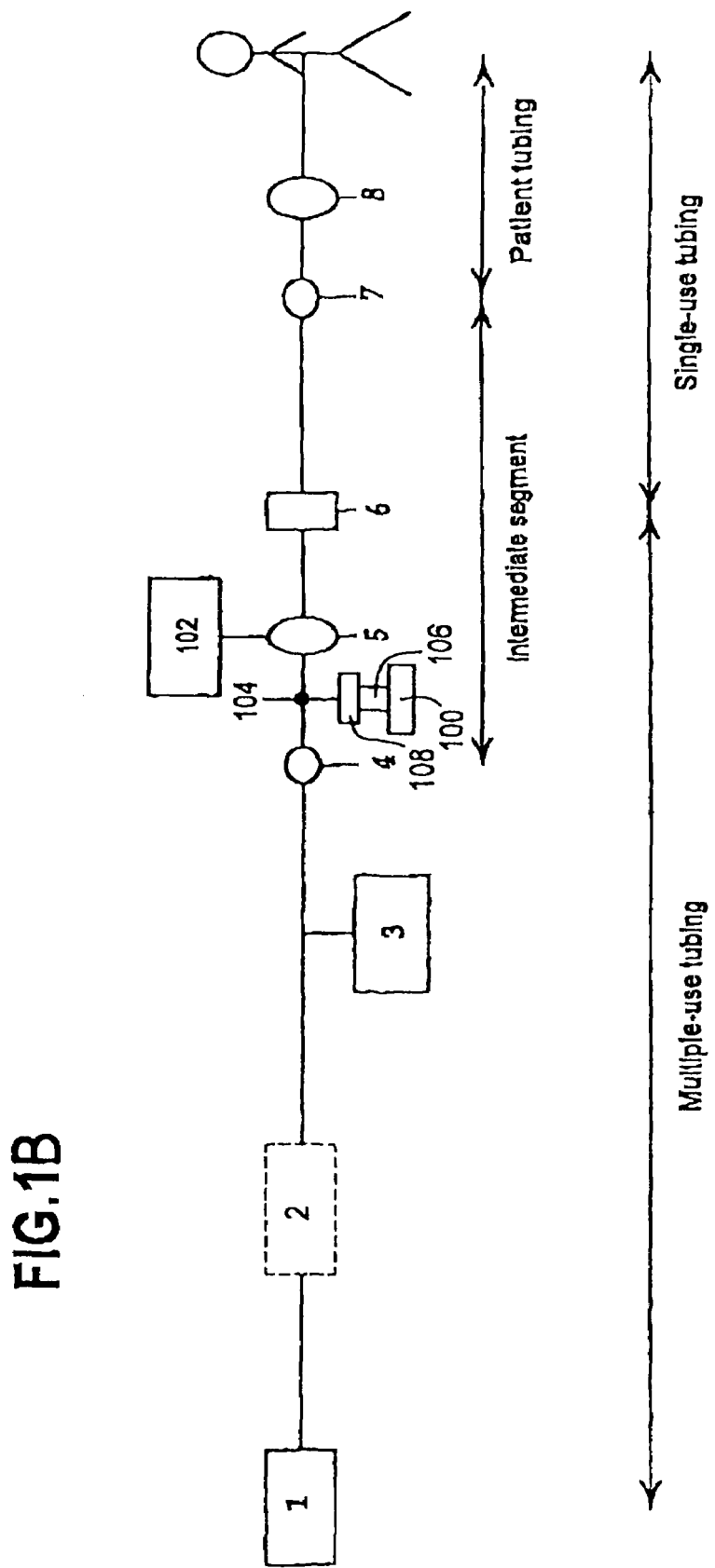
FIG. 1B is a diagram showing an alternative embodiment of the invention.

The liquid injection device in one embodiment (FIG. 1A) is constituted essentially by a piece of tubing, a reservoir 1, a pump system 2, an intermediate chamber 3 of variable volume, a regulation system 4 which may include the wheels of a peristaltic pump, and a non-return valve 7. A disconnection system 6 is situated upstream from the non-return valve 7, between said valve and the regulation system. Pressure sensors 5 and 8 are situated downstream and upstream from the non-return valve.

In the absence of injection, i.e. when the pump is deactivated, constant pressure exists between the non-return valve and the second regulation system. The constant pressure is lower than the opening pressure of the non-return valve.

If the non-return valve is defective, backflow of liquid towards the pump is prevented by the flow of liquid associated with the pressure that exists in the intermediate segment, with this pressure in the intermediate segment being due to the presence of the peristaltic cassette which, in the absence of injection, is very effective at occluding the tubing. The opening pressure of the occlusion system constituted by the wheels of the peristaltic cassette is greater than 8 bars, whereas the opening pressure of the first occlusion system is equal to 0.5 bars.

The present invention is naturally not limited solely to the example described above, with all configurations of the description also being included.

Thus, and preferably, the first occlusion system, or the regulation system, or both of them, are of the automatic clamp type. It is also possible to use a fourth occlusion device, preferably located downstream from the disconnection system, which device is activated in the event of an alarm being triggered.

The device of the present invention can also include a pressure sensor measuring the pressure of the liquid in a length of tubing situated upstream from the intermediate segment.

Figure 2A:
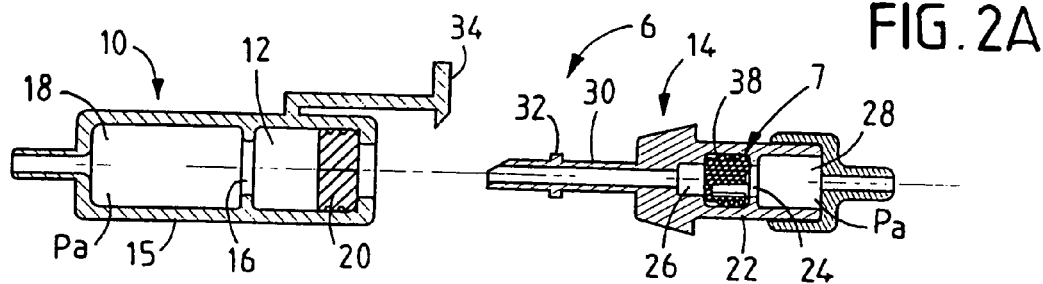
FIGS. 2A to 2I show various steps in the operation of a preferred disconnection system in its first use.

With reference to FIG. 2A, a preferred disconnection system 6 comprises an upstream piece 10 having an intermediate chamber 12 of adjustable volume, and a downstream piece 14 provided with the non-return valve 7 and capable of co-operating in reversible manner with the upstream piece 10 so as to form a sealed link.

The upstream piece 10 is constituted by a hollow tubular body 15 that is open at both ends, defining an inside volume that is split into two by an open internal radial wall 16 placed between an injection chamber 18 and the intermediate chamber 12 of adjustable volume, constituting a decompression chamber as explained below.

The intermediate chamber 12 contains a pre-split resilient septum 20 whose diameter is substantially equal to the inside diameter of the intermediate chamber 12 so as to form a piston that is movable in translation.

The downstream piece 14 comprises a hollow circularly-symmetrical body 22 that is extended at its two open ends by respective hollow rods. The body 22 surrounds an inside volume which is split in two by an open radial wall 24 placed between a first chamber 26 in which the non-return valve 7 is formed, and a second chamber 28 facing towards the patient.

Figure 2B:
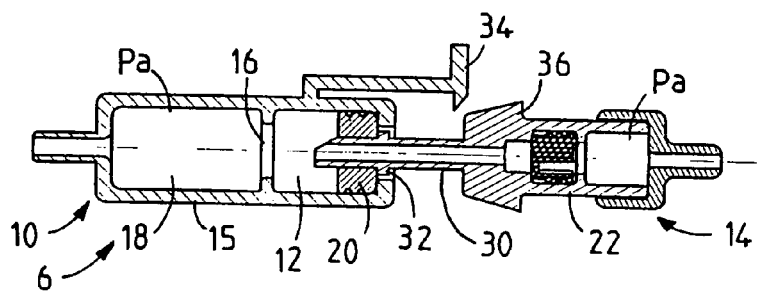
Figure 2C:
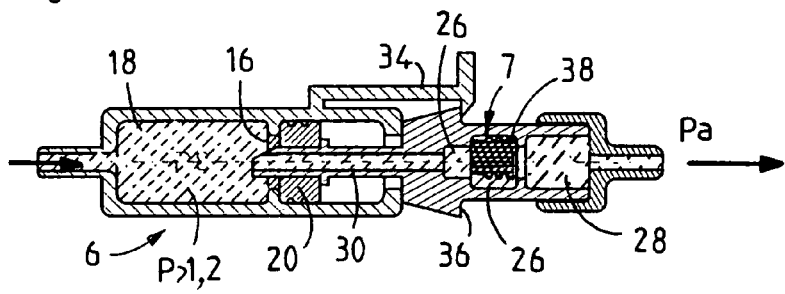
Figure 2D:
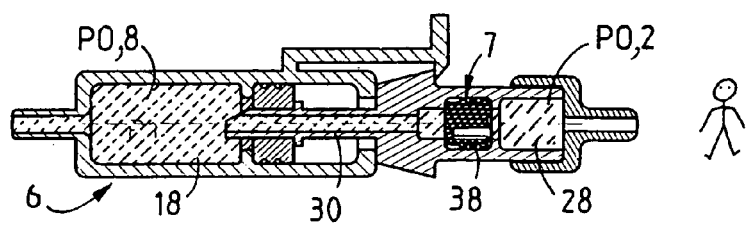

The hollow rod 30 adjacent to the first chamber 26 has a free end whose shape includes a frustoconical portion, and it is designed to be placed inside the intermediate chamber 12 by passing through the septum 20 and the opening of the wall 16. The hollow rod 30 has an outer annular collar 32 that comes into abutment against the septum 20 so as to drive it in translation inside the intermediate chamber 12 (FIG. 2B), the septum 20 coming into abutment against the wall 16 when the rod 30 is pushed home fully into the piece 10, the tubular body 15 then coming into abutment against the body 22 (FIG. 2C).

Locking means are also provided between the pieces 10 and 14, e.g. in the form of a resilient locking tab situated outside the body 15 and having a free end that snap-fastens against a shoulder or a groove in the outside surface of the body 22. Such a tab 34 is shown in FIG. 2B in association with a shoulder that faces in the opposite direction to the hollow rod 30 when the bodies 15 and 22 are in abutment.

A non-return valve 7 shown is formed by a plug 38 that is capable of being compressed (collapsing) radially enabling it to be bypassed by the liquid when the pressure of the liquid upstream from the plug 38 is greater than or equal to the opening pressure of the non-return valve 7.

This type of plug is preferably as described in U.S. Pat. No. 4,929,230, i.e. a plug made of resilient material of longitudinal section that can be seen in FIGS. 2A to 2I and 2'A, 2'B, and even more clearly in FIG. 3. The plug 38 has a first end directed towards the second chamber 28 with sealing means 46 that co-operate with the inside surface of the second chamber 28, a second end directed towards the hollow rod 30, at least one frustoconical surface portion 40 between the sealing means and the second end, and a cavity 42 extending inside said plug said first end and over a depth that is greater than the distance between the sealing means and the free edge of the first end. This plug 38 also has a retractable wall 44 between at least a portion of said frustoconical surface 40 and said cavity 42, said retractable wall 44 extending at least from the end of said cavity 42 as far as first end and retracting into said cavity 42 when the radial resultant of the pressure exerted on said frustoconical surface 40 by said liquid is greater than the sum of the radial compression strength of the retractable wall 44 plus the internal pressure of the cavity 42.

This type of plug 38 can also be placed in the tubing as a second occlusion system 4.

In a preferred embodiment, the opening pressure of the non-return valve 7 is greater than its closing pressure. By way of example, the plug 38 can be shaped so that it is compressed, thereby opening the valve 7, starting from a pressure of 1.2 bars for the liquid in the hollow rod 30, the retractable wall 44 returning to its initial shape and thus closing the valve 7 when the pressure of the liquid in the hollow rod is equal to or less than 0.8 bars.

Prior to any injection (FIGS. 2A and 2B) the pieces 10 and 14 of the connection system 6 are empty of liquid, i.e. they have atmospheric pressure (Pa) within them.

In general, throughout the description below, when said atmospheric pressure Pa is not mentioned, it should be assumed that it is to be added to the liquid pressure mentioned.

After the pieces 10 and 14 have been connected together, the injection device is primed (FIG. 2C) by sending liquid at a pressure greater than 1.2 bars (P>1.2) into the injection chamber 18. This liquid passes along the hollow rod 30, the septum 20 closing the intermediate chamber 12 in sealed manner, which chamber presents substantially zero volume in communication with the injection chamber 18. Because of this pressure of 1.2 bars which is greater than the opening pressure of the valve 7, the valve is opened and the liquid can pass through the first chamber 26 and leave the second chamber 28 in communication with the outside (Pa).

The following step (FIG. 2D) consists in stopping the delivery of liquid under pressure, the injection chamber 18 then being filled with a liquid at a pressure of about 0.8 bars (P0.8) causing the valve 7 to close by virtue of the retractable wall 44 returning to its initial position.

Once the valve 7 has closed, the injection device is connected to the patient so that the patient's venous pressure which is close to 0.2 bars (P0.2) corresponds substantially to the pressure of the liquid in the second chamber 28.

During injection (FIG. 2E), the pressure of the liquid in the disconnection system 6 is greater than 1.2 bars (P8), thereby holding the valve 7 open.

Figure 2E:
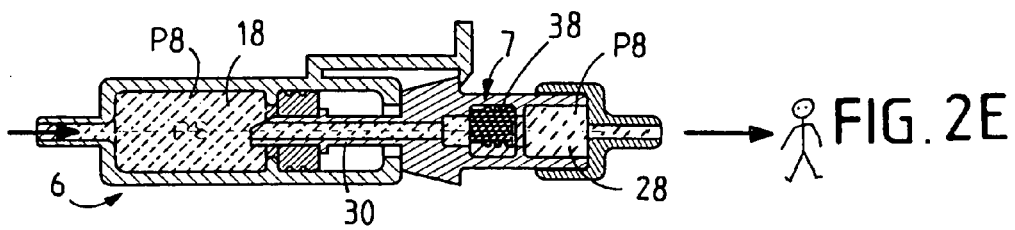
Figure 2F:
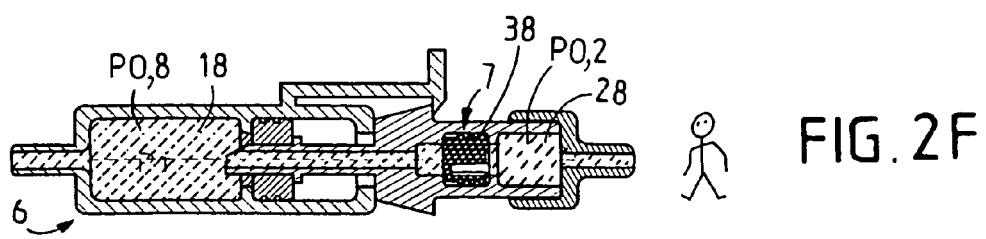
Figure 2G:
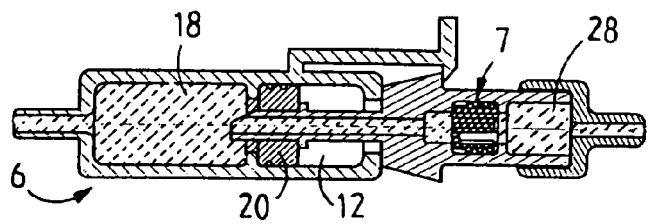
Figure 2H:
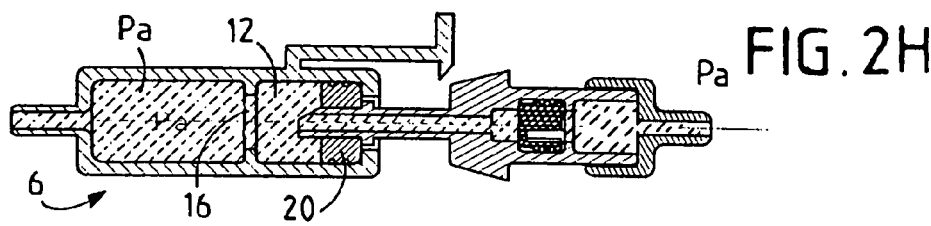
Figure 2I:
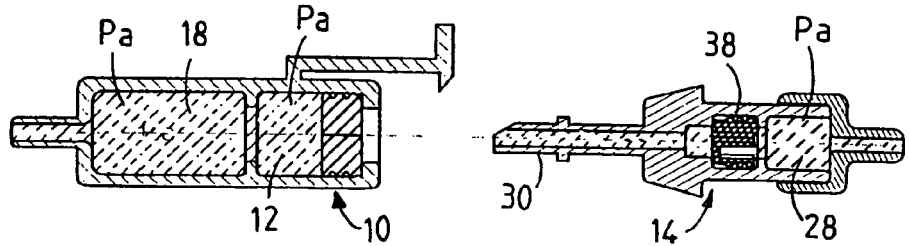
Figure 3:
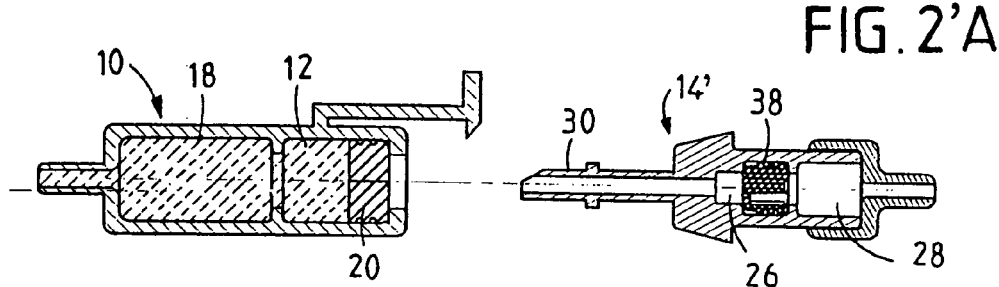
FIG. 3 is a longitudinal section of a preferred embodiment of a non-return valve.
Figure 3:
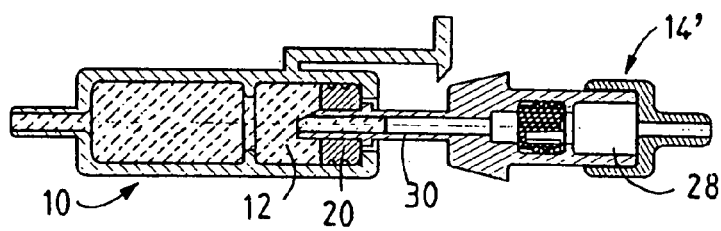
Figure 3:
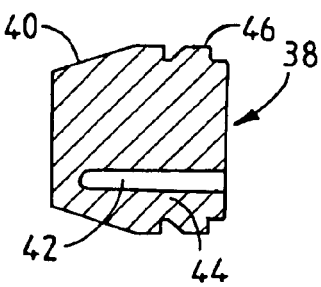
Figure 5:
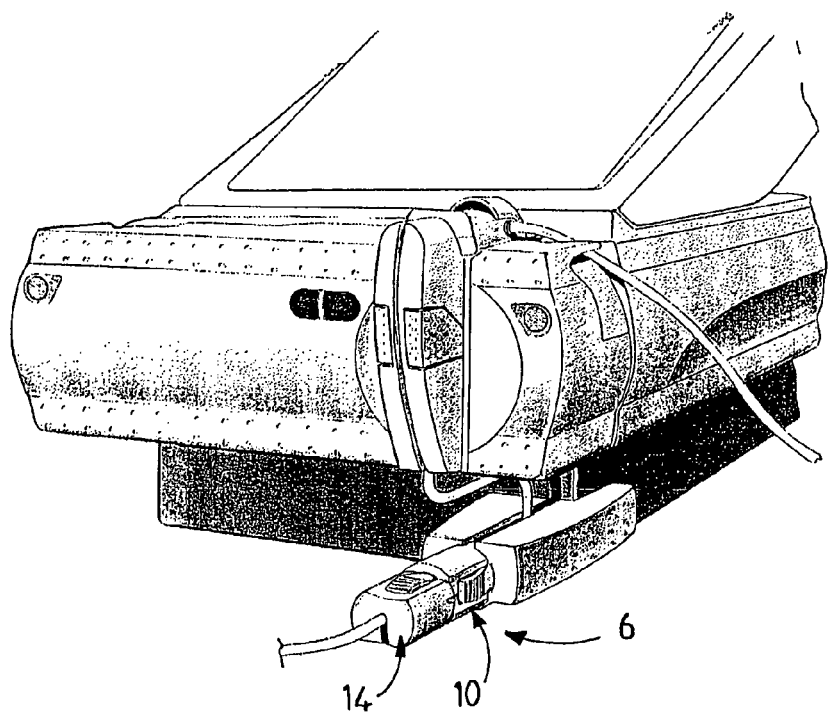
FIGS. 4 and 5 are perspective views of the disconnection system of FIGS. 2A to 2I, 2'A, and 2'B, respectively before and after connection to a liquid injection device, downstream from a peristaltic cassette.
Figure 4:
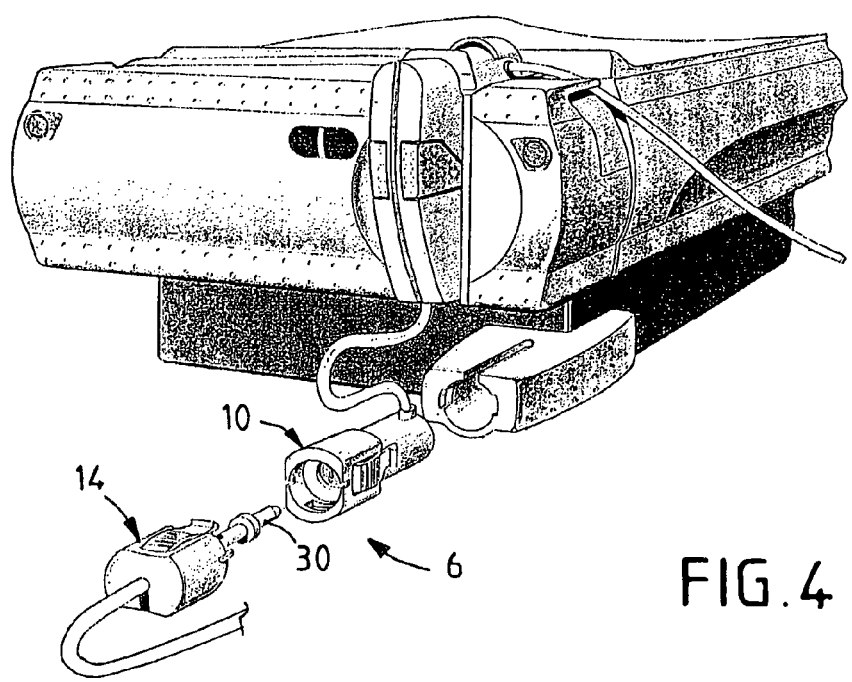

Once injection is over (FIG. 2F) the situation of the disconnection system 6 is identical to its situation (FIG. 2D) preceding the injection step (FIG. 2E).

When the patient is disconnected (FIG. 2G) from the injection device, the valve 7 remains closed, since the pressure of the liquid in the second chamber 28 is substantially zero (ignoring atmospheric pressure) and the pressure of the liquid in the injection chamber 18 is substantially of the order of 0.8 bars.

Thus, when the pieces 10 and 14 of the disconnection system 6 are moved apart (FIG. 2H), as the hollow rod 30 is withdrawn and the collar 32 moves away from the wall 16, the septum 20 also moves away from the wall 16 since the liquid pressure in the injection chamber 18 is greater than the pressure inside the second chamber 28.

The volume of the chambers 12 and 18 is designed to enable the septum 20 to move far enough away from the wall 16 to enable the pressure in the chambers 12 and 18 to drop to the level of atmospheric pressure so that the two pieces 10 and 14 can be separated (FIG. 2I) without any risk of liquid flowing out from the second chamber 28 or from the hollow rod 30. It will be understood that the internal volume of said upstream piece 18 is shaped so as to make it possible to obtain liquid pressure in the disconnection system 6 which is less than or equal to atmospheric pressure prior to said upstream and downstream pieces 10 and 14 being separated fully.

Because of this disconnection system, the plug 38 prevents the liquid that has filled the second chamber 28 and that has been in communication with the tubing connected to the patient from flowing back upstream. In addition, any outflow of liquid is avoided when the pieces 10 and 14 are disconnected.

When the injection device is used on a new patient, a new downstream piece 14' is used which is connected to the upstream piece 10 that has already been used on a preceding patient (FIGS. 2'A and 2'B). The subsequent steps in performing injection are identical to the steps illustrated by FIGS. 2C to 2I as already described.

What is claimed is:

1. A method for injecting liquid under pressure to a patient, the method comprising:

providing liquid under pressure to a patient through a length of tubing, the tubing including a pressurizing system, a first occlusion system and a regulation system located upstream from the first occlusion system, the first occlusion system and the regulation system defining an intermediate segment having an intermediate pressure, the tubing also including a segment downstream of the first occlusion system having a downstream pressure;

wherein due to the action of the pressurizing system, there is a positive pressure during the injection in the intermediate segment and the downstream segment; and when injection to the patient is desired to be stopped, closing the regulation system and the first occlusion system in such a manner that the first occlusion system closes when the pressure in the intermediate segment falls below an opening pressure of the first occlusion system, said opening pressure of the first occlusion system being greater than a venous pressure of the patient which corresponds to a maximum pressure of the downstream segment in the absence of injection, so that part of said positive pressure is maintained in the intermediate segment, while the pressure in the downstream segment is not maintained at such positive pressure, at least until the patient is disconnected from the tubing, in order to direct leakage of fluid from the first occlusion system to the patient.

2. The method according to claim 1, further comprising measuring the intermediate pressure in the intermediate segment in the absence of injection to the patient; and providing an output indicative of any leakage from the intermediate segment.

3. The method according to claim 2, further comprising activating an alarm in response to an output indicative of a leakage of liquid from the intermediate segment.

4. The method according to claim 2, further comprising responsive to the output indicative of a leakage from the intermediate segment, maintaining the intermediate pressure greater than the downstream pressure.

5. The method according to claim 4, wherein maintaining the intermediate pressure comprises activating a pump.

6. The method according to claim 1, wherein the intermediate segment includes a disconnection system having an upstream piece for multiple use and a downstream piece for single use, the method further comprising disconnecting the upstream piece from the downstream piece.

7. The method according to claim 6, further comprising decreasing in a controlled manner the intermediate pressure in the intermediate segment prior to disconnecting the upstream piece from the downstream piece to reduce leakage of liquid after disconnection.

8. The method according to claim 1, further comprising providing an opening pressure of the regulation system greater than the opening pressure of the first occlusion system to prevent any fluids in the intermediate segment from moving upstream through the regulation system.

9. The method according to claim 1, wherein the regulation system includes a non-return valve.

10. The method according to claim 1, wherein said maximum pressure is close to 0.2 Bar.

11. The method according to claim 1, wherein said maximum pressure is at least 0.2 Bar.

12. The method according to claim 1, wherein said opening pressure of the first occlusion system is greater than 0.2 Bar and equal to or less than 0.8 Bar.

13. The method according to claim 1, wherein said opening pressure of the first occlusion system is about 0.5 Bar.

* * * * *